United States Patent
Schmitt

(10) Patent No.: US 12,077,514 B2
(45) Date of Patent: *Sep. 3, 2024

(54) METHOD FOR RACEMISATION OF (5R)-4-[5-(3,5-DICHLOROPHENYL)-5-(TRIFLUOROMETHYL)-4H¬ISOXAZOL-3-YL]-2-METHYL-BENZOIC ACID

(71) Applicant: Intervet Inc., Madison, NJ (US)

(72) Inventor: Harald Schmitt, Mainz (DE)

(73) Assignee: Intervet Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/414,214

(22) PCT Filed: Dec. 20, 2019

(86) PCT No.: PCT/EP2019/086634
§ 371 (c)(1),
(2) Date: Jun. 15, 2021

(87) PCT Pub. No.: WO2020/127944
PCT Pub. Date: Jun. 25, 2020

(65) Prior Publication Data
US 2022/0041564 A1     Feb. 10, 2022

(30) Foreign Application Priority Data
Dec. 21, 2018  (EP) .................... 18215357

(51) Int. Cl.
*C07D 261/04*    (2006.01)
*C07B 55/00*    (2006.01)

(52) U.S. Cl.
CPC ............ *C07D 261/04* (2013.01); *C07B 55/00* (2013.01)

(58) Field of Classification Search
CPC .................................................. C07D 261/04
See application file for complete search history.

(56) References Cited

U.S. PATENT DOCUMENTS

2007/0066617 A1    3/2007  Mita et al.

FOREIGN PATENT DOCUMENTS

| JP | 2011051977 A | * | 3/2011 |
| JP | 2011051977 A |   | 3/2011 |
| WO | 2014090918 A1 |  | 6/2014 |

OTHER PUBLICATIONS

Reichardt "Empirical Parameters of Solvent Polarity as Linear Free-Energy Relationships" Angew. Chemie Int. Ed. Engl. 1979, 18, 98-110.*
Ceron-Carrasco, Jose P. et al, Solvent polarity scales: determination of new ET(30) values for 84 organic solvents, Journal of Physical Organic Chemistry, 2014, 512-518, 27.
Potapov, V.M. et al., Stereochemistry, Publishing House Moscow, 1976, 114, machine translation.
Potapov, V.M. et al., Stereochemistry, Publishing House Moscow, 1976, 114.
Sakai, Kenichi, Change in crystal habt of diastereomeric salt crystals in optical resolution using crystallization method and its utilization—Production of high optical purity 1-phenylethylamine, Journal of the Society of Organic Synthetic Chemistry, 57(5), 458-465, 1999.

* cited by examiner

Primary Examiner — David K O'Dell
(74) Attorney, Agent, or Firm — David J. Kerwick

(57) ABSTRACT

The present invention relates to a method for racemizing (5R)-4-[5-(3,5-dichlorophenyl)-5-(trifluoromethyl)-4H-isoxazol-3-yl]-2-methyl-benzoic acid.

8 Claims, No Drawings

METHOD FOR RACEMISATION OF (5R)-4-[5-(3,5-DICHLOROPHENYL)-5-(TRIFLUOROMETHYL)-4H-ISOXAZOL-3-YL]-2-METHYL-BENZOIC ACID

CROSS-REFERENCE TO RELATED APPLICATIONS

This application is a national stage entry under 35 U.S.C. § 371 of PCT/EP2019/086634 filed on Dec. 20, 2019, which claims priority to EP18215357.7 filed on Dec. 21, 2018, the content of PCT/EP2019/086634 is hereby incorporated by reference in its entirety.

The present invention relates to a method for racemizing (5R)-4-[5-(3,5-dichlorophenyl)-5-(trifluoromethyl)-4H-isoxazol-3-yl]-2-methyl-benzoic acid.

BACKGROUND OF THE INVENTION (5RS)-4-[5-(3,5-dichlorophenyl)-5-(trifluoromethyl)-4H-isoxazol-3-yl]-N-[2-oxo-2-(2,2,2-trifluoroethylamino)ethyl]-2-methyl-benzamide (hereinafter referred to as fluralaner) is a synthetic insecticide which is represented by the following Formula (A).

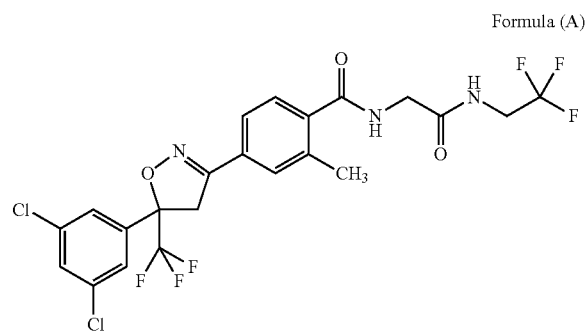 [SMILES: Cc1cc(C2=NOC(c3cc(Cl)cc(Cl)c3)(C(F)(F)F)C2)ccc1C(=O)NCC(=O)NCC(F)(F)F]

Formula (A)

Fluralaner is a systemic active ingredient that can be administered orally. The active ingredient is reported to antagonistically inhibit the GABA-gated chloride in the nervous system of several arthropods. Since fluralaner does not show an analogous bonding in the nervous systems of mammals, it is for example suitable for flea, mite and tick treatment in mammals, for example in dogs and cats.

Fluralaner is a racemate. The (S)-enantiomer is reported to be the eutomer substantially contributing to the antiparasitic activity of the active ingredient. In view thereof, the use of enantio-pure or enantio-enriched (S)-fluralaner is considered to be advantageous in comparison to racemic fluralaner. For preparing said enantio-pure or enantio-enriched (S)-fluralaner an enantio-pure or enantio-enriched (5RS)-4-[5-(3,5-dichlorophenyl)-5-(trifluoromethyl)-4H-isoxazol-3-yl]-2-methyl-benzoic acid acid (IOBA) is a key intermediate in the synthesis of fluralaner and said compound is represented by the following Formula (1)

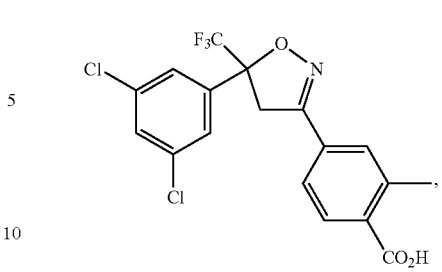

Formula (1)

wherein the compound according to Formula (1) can for example be prepared as described in synthetic example 3 of US 2007/0066617.

Since enantio-pure or enantio-enriched (S)-fluralaner might be considered as advantageous as active ingredient, the isolation of an enantio-pure or enantio-enriched (5S)-4-[5-(3,5-dichlorophenyl)-5-(trifluoromethyl)-4H-isoxazol-3-yl]-2-methyl-benzoic acid (S)-IOBA would be desirable.

When separating enantio-pure or enantio-enriched (S)-IOBA from the racemate (IOBA), a fraction containing enantio-pure or enantio-enriched (R)-IOBA would be left over. Compared to the preparation of IOBA, the racemisation of an enantio-pure or enantio-enriched (R)-IOBA as a by-product of the above separation would be highly desirable.

WO 2014/090918 A1 describes the separation of another compound, namely racemic 3-methyl-5-[(5RS)-5-(3,4,5-trichlorophenyl)-5-(trifluoromethyl)-4H-isoxazol-3-yl]thiophene-2-carboxylic acid (IOTA) into the enantiomer via chiral column chromatography or via diastereomeric recrystallisation. More particularly, said document describes that racemic IOTA is treated with (R)-1-(4-methylphenyl)ethylamine in a ternary mixture of water, acetonitrile and 2-butanol to obtain a precipitate of the corresponding (S)-IOTA salt with, after washing, a chiral purity of over 95%, which can be enhanced to over 98% by a further recrystallisation step. Further, the solution supernatant to the precipitate of the corresponding (S)-IOTA salt is removed under vacuum to obtain the valuable by-product, an enriched (R)-IOTA-mixture. This enriched (R)-IOTA-mixture is racemized with aqueous sodium hydroxide in toluene as solvent mixture at 75° C. in the presence of a phase-transfer catalyst, aqueous solution of tributyl methylammonium chloride.

The prior art process requires a ternary mixture of solvents for the precipitation of the (S)-enantiomer compound. This ternary solvent mixture, however, has to be changed for the racemisation of the remaining "by-product" enantio-enriched (R)-isoxazoline thiophene carboxylic acid. Moreover, the reaction of the prior art requires a phase transfer catalysts which are reported to be difficult to remove from the reaction mixtures and/or the desired products such that complex purification steps might be needed.

Furthermore, it was found that treating racemic IOBA with (R)-1-(4-methyl-phenyl)ethylamine did not result in any precipitation of (S)-IOBA and thus also not to a resolution of an enantio-pure or enantio-enriched (R)-IOBA.

Thus, there still exists a need for a racemisation of enantio-pure or enantio-enriched (5R)-4-[5-(3,5-dichlorophenyl)-5-(trifluoromethyl)-4H-isoxazol-3-yl]-2-methyl-benzoic acid which can preferably be applied in a simple and effective manner.

Hence, it is an object of the present invention to overcome one or more of the drawbacks of the above-mentioned processes. In particular, it is an object of the present invention to provide a method for racemising enantio-pure or enantio-enriched (5R)-4-[5-(3,5-dichlorophenyl)-5-(trifluoromethyl)-4H-isoxazol-3-yl]-2-methyl-benzoic acid without the need of complex purification steps. It is further an object of the present invention to provide a method for racemising enantio-pure or enantio-enriched (5R)-4-[5-(3,5-dichlorophenyl)-5-(trifluoromethyl)-4H-isoxazol-3-yl]-2-methyl-benzoic acid with a simple solvent system.

The present invention has unexpectedly solved at least one of the above objectives by the provision of a new synthetic approach for racemisation of a mixture containing (R)-IOBA and (S)-IOBA, wherein the mixture has an enantiomeric excess of (R)-IOBA.

Hence, the subject of the present invention is a method of racemizing a mixture containing (R)-4-[5-(3,5-dichlorophenyl)-5-(trifluoromethyl)-4H-isoxazol-3-yl)]-2-methyl-benzoic acid according to Formula (1a) and (S)-4-[5-(3,5-dichlorophenyl)-5-(trifluoromethyl)-4H-isoxazol-3-yl)]-2-methyl-benzoic acid according to Formula (1b)

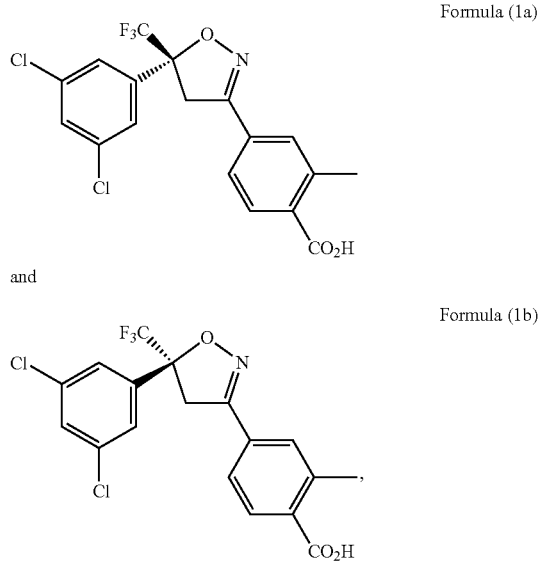

Formula (1a)

and

Formula (1b)

wherein the mixture has an enantiomeric excess of the compound according to Formula (1a) comprising the step of: (i) reacting the mixture with an alkaline compound in an organic solvent to obtain a reacted mixture.

DETAILED DESCRIPTION OF THE INVENTION

The present invention relates to a method for racemizing a mixture containing (5R)-4-[5-(3,5-dichlorophenyl)-5-(trifluoromethyl)-4H-isoxazol-3-yl]-2-methyl-benzoic acid ((R)-IOBA) according to Formula (1a) and (5S)-4-[5-(3,5-dichlorophenyl)-5-(trifluoromethyl)-4H-isoxazol-3-yl]-2-methyl-benzoic acid ((S)-IOBA) according to Formula (1b), wherein in the mixture comprises an enantiomeric excess of the compound according to Formula (1a).

In line with the present application racemizing is considered as shifting the enantiomeric excess of a compound to a lower value. Racemizing is not strictly considered as shifting the enantiomeric value to 0, which is the literal meaning of a racemate.

Generally, the enantiomeric excess (ee) can be determined as described below. It may range from 1 to 100%, preferably 10 to 100%, more preferably 25 to 100%, in particular 50 to 100%.

An enantiomeric excess of the compound according to Formula (1a) means that the mixture comprises a higher amount of the compound according to Formula (1a) than the compound according to Formula (1b).

In an embodiment of the invention and/or embodiments thereof the enantiomeric excess of the compound according to Formula (1a) can be 100%; i.e. the mixture contains just the compound according to Formula (1a), but no compound according to Formula (1b).

The compounds according to Formulae (1a) and (1b) are the (R)-enantiomer or the (S)-enantiomer of the compound according to Formula (1), (5RS)-4-[5-(3,5-dichlorophenyl)-5-(trifluoromethyl)-4H-isoxazol-3-yl]-2-methyl-benzoic acid.

In step (i) of the method according to the invention and/or any embodiment thereof the mixture containing (R)-IOBA according to Formula (1a) and (S)-IOBA according to Formula (1b) is reacted with an alkaline compound in an organic solvent.

In line with the present application an alkaline compound in step (i) can be considered as base, which according to Broensted is a compound that can accept hydrogen cations.

An alkaline compound can be an organic or an inorganic alkaline compound.

Examples of organic alkaline compounds are diisopropylethylamine (DIPEA), 1,8-diazabicyclo[5.4.0]undec-7-ene (DBU), 1,5-diazabicyclo[4.3.0]non-5-eand 2-tert-btuyimino-2-dietalamino-1,3-dimethylperhydro-1,3,2-diazaphosphorine and mixtures thereof.

In a preferred embodiment of the invention and/or embodiments thereof the alkaline compound in step (i) is an inorganic compound.

Examples of suitable inorganic alkaline compounds are alkali or earth alkali phosphates, alkali or earth alkali carbonates, alkali or earth alkali hydrogen carbonates, alkali or earth alkali hydroxides, alkali or earth alkali oxides or mixtures thereof.

In a preferred embodiment of the invention and/or embodiments thereof the alkaline compound in step (i) can be selected from the group consisting of lithium oxide, sodium oxide, potassium oxide, cesium oxide, lithium hydroxide, sodium hydroxide, potassium hydroxide, cesium hydroxide, calcium hydroxide barium hydroxide, magnesium oxide, calcium oxide, barium oxide, cesium carbonate and mixtures thereof. Preferred are sodium hydroxide, potassium hydroxide, cesium hydroxide, calcium hydroxide, barium hydroxide, barium oxide and mixtures thereof.

In a preferred embodiment of the invention and/or embodiments thereof the alkaline compound in step (i) can be selected from the group consisting of sodium hydroxide, potassium hydroxide, cesium hydroxide and mixtures thereof.

Further alkaline compound suitable to be used in step (i) are alkali or earth alkali alkoholates. Suitable examples are sodium methanolate, potassium methanolate, sodium ethanolate, potassium ethanolate, sodium tert.butylate and potassium tert.butylate and mixtures thereof.

Step (i) of the present method is carried out in an organic solvent. Organic solvents are well known by those skilled in the art. Though not containing any carbon atom in line with the present application, water is considered as an organic solvent.

Suitable organic solvents are for example water, alcohols such as propanol, cyclic ethers such as tetrahydronfuran and dioxane, aliphatic esters such as ethyl acetate, unsubstituted or substituted benzols such as benzol and toluene.

In a preferred embodiment of the invention and/or embodiments thereof the organic solvent is selected from the group consisting of water, alcohol with 1 to 5 carbons atoms, tetrahydrofuran, dioxane, toluene, ethyl acetate and mixtures thereof, more preferred from the group consisting of water, alcohol with 2 to 5 carbons atoms, dioxane, toluene and mixtures thereof.

In a preferred embodiment of the invention and/or embodiments thereof the organic solvent in step (i) is an alcohol with 1 to 5 carbon atoms. The alcohol is preferably a mono alcohol, i.e. the organic solvent carries just one hydroxy group. It is further preferred that the organic solvent just carries the hydroxy functional group. In other words, the alcohol does not carry any other functional group apart from the (one) hydroxy group. Further, the alcohol with 1 to 5 carbon atoms used as organic solvent just contains hydrogen, oxygen and carbon atom(s). Suitably the alcohol is not further substituted.

Examples of alcohols with 1 to 5 carbon atoms used as organic solvent are methanol, ethanol, 1-propanol, 2-propanol, cyclopropyl alcohol, 1-butanol, 2-butanol, cyclobutanol, 2-methyl-1-propanol, 2-methyl-2-propanol, 1-pentanol, 2-pentanol, 3-pentanol, cyclopentanol, 2-methyl-1-butanol, 3-methyl-1-butanol, 3-methyl-2-butanol, 2-methyl-2-butanol, 2,2-dimethyl-1-propanol and mixtures thereof.

In a preferred embodiment of the invention and/or embodiments thereof the organic solvent is an alcohol with 1 to 5 carbon atoms selected from the group consisting of ethanol, 1-propanol, 2-propanol, 1-butanol, 2-butanol, 2-methyl-1-propanol, 1-pentanol, 2-pentanol, 3-pentanol and mixtures thereof. More preferably the organic solvent is an alcohol with 2 to 5 carbon atoms selected from the group consisting ethanol, 1-propanol, 2-propanol, 1-butanol, 1-pentanol and mixtures thereof.

In a particularly preferred embodiment of the invention and/or embodiments thereof the organic solvent in step (i) is ethanol.

In a preferred embodiment of the invention and/or embodiments thereof in step (i) the organic solvent is ethanol and the alkaline compound is sodium hydroxide.

In a preferred embodiment of the invention and/or embodiments thereof in step (i) the organic solvent is ethanol and the alkaline compound is potassium hydroxide.

In a preferred embodiment of the invention and/or embodiments thereof in step (i) the organic solvent is ethanol and the alkaline compound is cesium hydroxide.

In a preferred embodiment of the invention and/or embodiments thereof in step (i) the organic solvent is ethanol and the alkaline compound is calcium hydroxide.

In a preferred embodiment of the invention and/or embodiments thereof in step (i) the organic solvent is ethanol and the alkaline compound is barium hydroxide.

In a preferred embodiment of the invention and/or embodiments thereof in step (i) the organic solvent is ethanol and the alkaline compound is barium oxide.

In a particularly preferred embodiment of the invention and/or embodiments thereof the organic solvent in step (i) is 1-propanol.

In a preferred embodiment of the invention and/or embodiments thereof in step (i) the organic solvent is 1-propanol and the alkaline compound is sodium hydroxide.

In a preferred embodiment of the invention and/or embodiments thereof in step (i) the organic solvent is 1-propanol and the alkaline compound is potassium hydroxide.

In a preferred embodiment of the invention and/or embodiments thereof in step (i) the organic solvent is 1-propanol and the alkaline compound is cesium hydroxide.

In a preferred embodiment of the invention and/or embodiments thereof in step (i) the organic solvent is 1-propanol and the alkaline compound is calcium hydroxide.

In a preferred embodiment of the invention and/or embodiments thereof in step (i) the organic solvent is 1-propanol and the alkaline compound is barium hydroxide.

In a preferred embodiment of the invention and/or embodiments thereof in step (i) the organic solvent is 1-propanol and the alkaline compound is barium oxide.

In a particularly preferred embodiment of the invention and/or embodiments thereof the organic solvent in step (i) is 2-propanol.

In a particularly preferred embodiment of the invention and/or embodiments thereof in step (i) the organic solvent is 2-propanol and the alkaline compound is sodium hydroxide.

In a particularly preferred embodiment of the invention and/or embodiments thereof in step (i) the organic solvent is 2-propanol and the alkaline compound is potassium hydroxide.

In a particularly preferred embodiment of the invention and/or embodiments thereof in step (i) the organic solvent is 2-propanol and the alkaline compound is cesium hydroxide.

In a particularly preferred embodiment of the invention and/or embodiments thereof in step (i) the organic solvent is 2-propanol and the alkaline compound is calcium hydroxide.

In a particularly preferred embodiment of the invention and/or embodiments thereof in step (i) the organic solvent is 2-propanol and the alkaline compound is barium hydroxide.

In a particularly preferred embodiment of the invention and/or embodiments thereof in step (i) the organic solvent is 2-propanol and the alkaline compound is barium oxide.

In a preferred embodiment of the invention and/or embodiments thereof the molar ratio of the mixture containing (R)-IOBA according to Formula (1a) and (S)-IOBA according to Formula (1b) to the alkaline compound is 1:1 to 1:10, more preferably 1:2 to 1:8, in particular 1:3 to 1:6, especially about 1:4.5

In a preferred embodiment of the invention and/or embodiments thereof step (i) is carried out at an elevated temperature. An elevated temperature is a temperature from 23° C. (room temperature) to the boiling temperature of the organic solvent. In a preferred embodiment of the invention and/or embodiments thereof step (i) is carried out at the boiling temperature of the organic solvent. All temperatures as indicated herein and relating to boiling temperatures or boiling points relate to temperatures measured at normal pressure of 101 kPa.

Further, the reaction of step (i) can be preferably subjected to a mechanical movement such as stirring or ultrasonic treatment.

In a preferred embodiment of the invention and/or embodiments thereof the duration of step (i) can be between 30 minutes and 48 hours, preferably between 2 hour and 36 hours, in particular between 4 hours and 24 hours.

In a preferred embodiment of the invention and/or embodiments thereof the present method further comprises the steps of
(ii) acidifying the reacted mixture from step (i) thereby obtaining a result mixture
(iii) separating the resulting mixture into a compound mixture and a supernatant.

In step (ii) the reacted mixture from step (i) can be acidified, preferably with an aqueous solution of a Broensted acid. In a preferred embodiment of the invention and/or embodiments thereof the acid has a pKa of 3.5 or less, preferably a pKa of 3.0 or less, more preferably a pKa of 2.5 or less, in particular a pKa of 2.0 or less.

Examples of suitable acids having a pKa of 3.5 or less are hydrogen chloride (the corresponding acid is hydrochloric acid), hydrogen bromide, hydrogen iodide, nitric acid, sulfuric acid, sodium or potassium hydrogen sulfate, phosphoric acid, trichloro acetic acid, fumaric acid, maleic acid, oxalic acid, citric acid, lactic acid, 2-chlorobenzoic acid, methanesulfonic acid, ethanesulfonic acid, p-toluene sulfonic acid and mixtures thereof.

A Bronsted acid can be an organic or an inorganic acid.

Examples of organic acids that can be used as Bronsted acids are fumaric acid, maleic acid, oxalic acid, citric acid, lactic acid, methanesulfonic acid, ethanesulfonic acid, p-toluene sulfonic acid and mixtures thereof. Preferred are methanesulfonic acid, ethanesulfonic acid and p-toluene sulfonic acid, in particular methanesulfonic acid and p-toluene sulfonic acid.

Examples of inorganic acids that can be used as Bronsted acids are hydrogen chloride (the corresponding acid is hydrochloric acid), hydrogen bromide, hydrogen iodide, nitric acid, sulfuric acid, sodium or potassium hydrogen sulfate, phosphoric acid and mixtures thereof.

In a preferred embodiment of the invention and/or embodiments thereof the acidic aqueous solution in step (ii) is a solution of an inorganic acid, preferably hydrogen chloride, hydrogen bromide, sulfuric acid, sodium or potassium hydrogen sulfate, phosphoric acid and mixtures thereof, more preferably hydrogen chloride, sodium or potassium hydrogen sulfate, phosphoric acid and mixtures thereof, in particular hydrogen chloride, potassium hydrogen sulfate, or phosphoric acid, especially potassium hydrogen sulfate.

Step (ii) of acidifying the solution from step (i) can preferably be carried under cooling, preferably at a temperature of 5° C. to 20° C., more preferably about 10° C.

Further, step (ii) can preferably be carried out under a mechanical movement such as stirring or an ultrasonic treatment.

In step (iii) the compound mixture can be separated. Said compound mixture contains (R)-IOBA according to Formula (1a) and (S)-IOBA according to Formula (1b), wherein in the amount of the (S)-IOBA according to Formula (1b) is enhanced in the mixture compared to the amount of (S)-IOBA in the mixture of step (i). In a preferred embodiment of the invention and/or embodiments thereof the resulting compound is the racemate of IOBA, i.e. (R)-IOBA according to Formula (1a) and (S)-IOBA according to Formula (1b) are present in a molar ration of about 1:1.

Separating can comprise well known methods for separating a solid organic compound, in particular a solid organic acid, from an acidic aqueous solution. Separating can comprise methods such decanting or pouring off the solution, optionally with a preceding centrifugation step, and filtration. Further, separating can be conducted via an extraction of the desired compound from the acidic aqueous solution.

In a preferred embodiment of the invention and/or embodiments thereof in step (iii) the separation of the resulting compound mixture is carried out by an extraction with an organic solvent. Organic solvents are well known by those skilled in the art. In step (iii) extraction can be preferably carried out in an aprotic organic solvent. Organic solvents suitable to be used in present step (iii) are for example toluene, benzene, xylene, ethyl acetate, hexane, heptane, octane, cyclic and acyclic alkylethers, chlorobenzene, cyclohexane, methylcyclohexane, dichloromethane, dichloroethane, trichloromethane, trichloroethane, tetrachloroethane, dimethoxyethane, diethoxyethane and combinations thereof. Preferred are ethyl acetate, toluene, dichloromethane and trichloromethane, in particular ethyl acetate and toluene, especially ethyl acetate.

The extraction step preferably comprises adding organic solvent to the acidified aqueous solution from step (ii), mixing the two liquids, separating the phase with the organic solvent from the acidic aqueous solution. This procedure can preferably be repeated, preferably repeated two to four times. Subsequently the organic phases can be preferably combined and dried. Drying can be conducted with any known drying agent such as sodium sulfate or magnesium sulfate. After drying the drying agent can be separated from the organic phase, preferably by filtration.

Further, step (iii) preferably comprises removing the organic solvent from the organic phase, preferably from the combined organic phase. Removing the organic solvent can preferably be conducted at a temperature of 23° C. to 50° C., preferably about 40° C. and/or at a reduced pressure of 1 kPa to 90 kPa, preferably about 10 kPa.

In a preferred embodiment of the invention and/or embodiments thereof step (i) is carried out in the absence of phase transfer catalysts. A phase transfer catalyst can be regarded as a substance that facilitates the migration of a reactant from one phase into another phase where reaction occurs. A phase transfer catalyst can also be regarded as a heterogenous catalyst. By avoiding the use of a phase transfer catalyst the purity of the desired product, in the present case the compound resulting from step (iii), can be enhanced, since a phase transfer catalyst is often difficult to remove from a reaction mixture and/or a desired product.

In a preferred embodiment of the invention and/or embodiments thereof the present method further comprises the preceding steps of (a) reacting (5RS)-4-[5-(3,5-dichlorophenyl)-5-(trifluoromethyl)-4H-isoxazol-3-yl]-2-methyl-benzoic acid with a compound of Formulae (2A), (2B) or (2C)

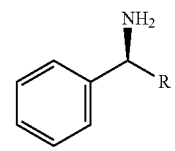

Formula (2A)

wherein R is an alkyl with 1 or 2 carbon atoms,

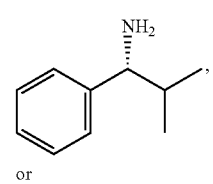

Formula (2B)

or

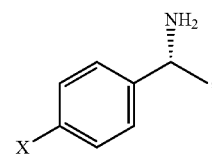

Formula (2C)

wherein X is Cl or Br, in an organic solvent selected from the group consisting of an organic solvent having a polarity $E_T(30)$ between 180 and 230 kJ/mol, an organic solvent having a polarity $E_T(30)$ between 130 and 175 kJ/mol and mixtures thereof to form a precipitate and a supernatant solution, and (b) separating the supernatant solution containing (5R)-4-[5-(3,5-dichlorophenyl)-5-(trifluoromethyl)-4H-isoxazol-3-yl]-2-methyl-benzoic acid according to Formula (1a) and (5S)-4-[5-(3,5-dichlorophenyl)-5-(trifluoromethyl)-4H-isoxazol-3-yl]-2-methyl-benzoic acid according to Formula (1b)

Formula (1a)

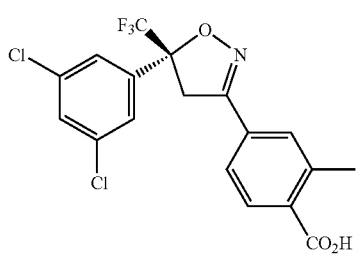

and

Formula (1b)

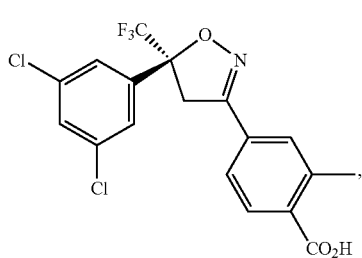

from the precipitate and a supernatant solution.

In a preferred embodiment of the invention and/or embodiments thereof the above-mentioned steps (a) and (b) can be carried out consecutively.

In a preferred embodiment of the invention and/or embodiments thereof the steps (a) and (b) as well as step (i) can be carried out consecutively.

In a preferred embodiment of the invention and/or embodiments thereof the steps (a) and (b) as well as steps (i), (ii) and (iii) can be carried out consecutively.

In a preferred embodiment of the invention and/or embodiments thereof in step (a) of the method according to the invention and/or any embodiment thereof (5RS)-4-[5-(3,5-dichlorophenyl)-5-(trifluoromethyl)-4H-isoxazol-3-yl]-2-methyl-benzoic acid is reacted with a compound of Formula (2A), (2B) or (2C) in an organic solvent selected from the group consisting of an organic solvent having a polarity $E_T(30)$ between 180 and 230 kJ/mol, an organic solvent having a polarity $E_T(30)$ between 130 and 175 kJ/mol and mixtures thereof to form a precipitate and a supernatant solution.

In Formula (2A) residue R is an alkyl with one or two carbon atoms.

In a preferred embodiment of the invention and/or embodiments thereof residue R is an alkyl with one carbon atom, i.e. residue R is methyl. The corresponding base or alkaline compound is (S)-1-phenylethylamine.

In an alternatively preferred embodiment of the invention and/or embodiments thereof residue R is an alkyl with two carbon atoms, i.e. residue R is ethyl. The corresponding base or alkaline compound is (S)-1-phenylpropylamine.

The compound according to Formula (2B) is (R)-1-phenyl-2-methyl-propylamine.

In Formula (2C) residue X is Cl or Br.

In a preferred embodiment of the invention and/or embodiments thereof residue X in Formula (2C) is Cl and the corresponding base or alkaline compound is (R)-1-(4-chlorophenyl)-ethylamine.

In a more preferred embodiment residue X in Formula (2C) is Br and the corresponding base or alkaline compound is (R)-1-(4-bromophenyl)-ethylamine.

In a preferred embodiment of the invention and/or embodiments thereof the compound of Formula (2A), (2B) or (2C) is selected from the group consisting of (S)-1-phenyl-propylamine, (R)-1-phenyl-2-methyl-propylamine, (R)-1-(4-chlorophenyl)-ethylamine and (R)-1-(4-bromophenyl)-ethylamine.

In a preferred embodiment of the invention and/or embodiments thereof (5RS)-4-[5-(3,5-dichlorophenyl)-5-(trifluoromethyl)-4H-isoxazol-3-yl]-2-methyl-benzoic acid is reacted in step (i) with a compound of Formula (2A), (2B) or (2C) in a molar ratio of between 1:0.4 and 1:5, preferably between 1:0.5 and 1:3, more preferably between 1:0.6 and 1:2, in particular between 1:0.7 and 1:1.

In step (a) an organic solvent is a liquid compound that dissolves, preferably completely dissolves, a substance to form a solution. Examples of organic solvents are well known in the art. Organic solvents can be classified in categories, for example with their boiling points (high or low boing solvents), their acidity/basicity (acidic or alkaline solvents) and/or their polarity (polar and non-polar solvents).

The $E_T(30)$ value is regarded to indicate the polarity of different solvents (see for example Jose P. Ceron-Carrasco et al.: "Solvent polarity scales: determination of new $E_T(30)$ values for 84 organic solvents", Research Article; Journal of Physical Organic Chemistry, 2014, 27, pages 512-518). The $E_T(30)$ value is determined with the help of the negative solvatochromic dye 2,6-diphenyl-4-(2,4,6-triphenylpyridin-1-ium-1-yl)phenolate, which is also referred to as Betaine 30 or Reichhardt's dye. Betaine 30 is represented by the compound according to below Formula (B)

Formula (B)

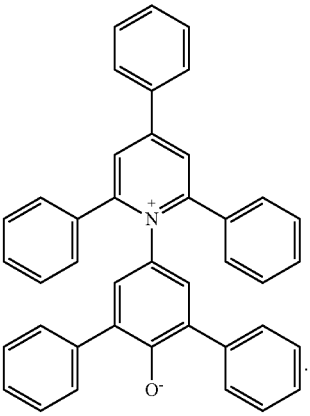

More specifically, the $E_T(30)$ value is determined with the help of Betaine 30 in the corresponding solvent through the longest wavelength VIS/NIR adsorption band. High $E_T(30)$ values are considered to correspond to a high polarity of the solvent, whereas low $E_T(30)$ values indicate low polarity of the solvent. Thus, in short, the higher the $E_T(30)$ value, the more polar the solvent and vice versa. The $E_T(30)$ value is also defined as the molar electronic excitation energy and calculated as follows $$E_T(30) = \frac{119627 \text{ kJ} \cdot \text{nm} \cdot \text{mol}^{-1}}{\lambda_{max}}$$

wherein $\lambda_{max}$ is the long-wavelength adsorption band in the visible/near IR-region of Betaine 30 in the corresponding solvent, when measured at 25° C. and 101 kPa.

In a preferred embodiment of the invention and/or embodiments thereof in step (a) of the present method the organic solvent has an $E_T(30)$ value between 170 and 230 kJ/mol, preferably between 180 and 225 kJ/mol, more preferably between 190 and 220 kJ/mol, in particular between 200 and 218 kJ/mol.

Examples of organic solvents having an $E_T(30)$ value between 170 and 230 kJ/mol are pyridines such as 2-fluoropyridine and 2,6-difluoropyridine; alcohols such as ethanol, 1-propanol, 2-propanol, cyclopropyl alcohol, 1-butanol, 2-butanol, cyclobutanol, 2-methyl-1-propanol, 2-methyl-2-propanol, 1-pentanol, 2-pentanol, 3-pentanol, cyclo-pentanol, 2-methyl-1-butanol, 3-methyl-1-butanol, 3-methyl-2-butanol, 2-methyl-2-butanol, 2,2-dimethyl-1-propanol, allyl alcohol, 2-methoxyethanol, 2-ethoxyethanol, 2-(n-butoxy) ethanol, 2-phenoxyethanol, cyclohexanol, 1-hexanol, 1-heptanol, 1-octanol, 1-nonanol, 1-decanol, 2-phenylethanol, benzyl alcohol, 2-chloroethanol, 1,1,1-tifluoro-2-(trifluoromethyl)pentan-2-ol, 1,1,1-tifluoro-2(trifluoromethyl)pent-4-en-2-ol, 2,2,2-trifluoro-1-phenylethanol, 1,1,1,3,3,3-hexafluoro-2-phenylpropan-2-ol; ketones such as 1,1,1-trichloracetone; esters and lactones such as 4-butyrolactone and ethyl propynoate; amides and cyanamides such as N,N-dimethylformamide, N,N-dimethyl cyanamide, pyrrolidine-2-one, N-methylpropionamide, N-ethylacetamide, N-methyl-acetamide, N-methylformamide; nitriles such as n-propanenitrile, 3-methoxypropane-nitrile, acetonitrile, chloracetonitrile; nitroalkane such as nitromethane and nitroethane; aromatic amines such as aniline; phosphorous compounds such as trimethyl phosphate; and sulphurous compounds such as tetrahydro-3-methylthiophene-1,1-dioxide, tetra-methylene sulfoxide, dimethyl sulfoxide and ethylene sulphite.

In a preferred embodiment of the invention and/or embodiments thereof the organic solvent in step (a) is an alcohol selected from ethanol, 1-propanol, 2-propanol, cyclopropyl alcohol, 1-butanol, 2-butanol, cyclobutanol, 2-methyl-1-propanol, 2-methyl-2-propanol, 1-pentanol, 2-pentanol, 3-pentanol, cyclopentanol, 2-methyl-1-butanol, 3-methyl-1-butanol, 3-methyl-2-butanol, 2-methyl-2-butanol, 2,2-dimethyl-1-propanol, allyl alcohol, 2-methoxyethanol, 2-ethoxyethanol, 2-(n-butoxy) ethanol, 2-phenoxyethanol, cyclohexanol, 1-hexanol, 1-octanol, 1-decanol, 2-phenylethanol, benzyl alcohol, 2-chlor-ethanol, 1,1,1-tifluoro-2-(trifluoromethyl) pentan-2-ol, 1,1,1-trifluoro-2-(trifluoromethyl)pent-4-en-2-ol, 2,2,2-trifluoro-1-phenylethanol, 1,1,1,3,3,3-hexafluoro-2-phenylpropan-2-ol and mixtures thereof.

In a preferred embodiment of the invention and/or embodiments thereof solvent the organic solvent in step (a) is an alcohol with 2 to 8 carbon atoms. The alcohol is preferably a monoalcohol, i.e. the organic solvent carries just one hydroxy group. It is further preferred that the organic solvent just carries the hydroxy functional group. In other words, the alcohol does not carry any other functional group apart from the (one) hydroxy group. Further, the alcohol with 2 to 8 carbon atoms used as organic solvent just contains hydrogen, oxygen and carbon atom(s). Suitably the alcohol is further not substituted.

Examples of alcohols with 2 to 8 carbon atoms used as organic solvent are ethanol, 1-propanol, 2-propanol, cyclopropyl alcohol, 1-butanol, 2-butanol, cyclobutanol, 2-methyl-1-propanol, 2-methyl-2-propanol, 1-pentanol, 2-pentanol, 3-pentanol, cyclo-pentanol, 2-methyl-1-butanol, 3-methyl-1-butanol, 3-methyl-2-butanol, 2-methyl-2-butanol, 2,2-dimethyl-1-propanol, 1-hexanol, 1-heptanol, 1-octanol and mixtures thereof.

In a preferred embodiment of the invention and/or embodiments thereof the organic solvent in step (a) is an alcohol with 2 to 8 carbon atoms selected from the group consisting of ethanol, 1-propanol, 2-propanol, 1-butanol, 2-butanol, 2-methyl-1-propanol, 1-pentanol, 2-pentanol, 3-pentanol, 1-hexanol and mixtures thereof, more preferably the organic solvent is an alcohol with 2 to 8 carbon atoms selected from the group consisting ethanol, 2-propanol, 1-butanol, 1-pentanol, 1-hexanol, 1-heptanol and mixtures thereof.

In a particularly preferred embodiment of the invention and/or embodiments thereof the organic solvent in step (a) is ethanol. In an alternatively preferred embodiment the organic solvent in step (a) is 2-propanol. In an alternatively preferred embodiment the organic solvent in step (a) is 1-butanol. In an alternatively preferred embodiment the organic solvent in step (a) is 1-pentanol. In an alternatively preferred embodiment the organic solvent in step (a) is 1-hexanol.

In a preferred embodiment of the invention and/or embodiments thereof the organic solvent in step (a) is not an amide or cyanamide.

In a preferred embodiment of the invention and/or embodiments thereof the organic solvent in step (a) is not a sulphurous compound.

In a preferred embodiment of the invention and/or embodiments thereof in step (a) residue R of Formula (2A)) is methyl and the organic solvent is selected from ethanol, 2-propanol, 1-butanol, 1-pentanol, 1-hexanol, 1-heptanol, 1-octanol and mixtures thereof.

Alternatively preferred, in step (a) residue R of Formula (2A) is methyl and the organic solvent is ethanol, or residue R of Formula (2A) is methyl and the organic solvent is 2-propanol.

Alternatively preferred, in step (a) residue R of Formula (2A) is methyl and the organic solvent is 1-butanol, or residue R of Formula (2A) is methyl and the organic solvent is 1-pentanol, or residue R of Formula (2A) is methyl and the organic solvent is 1-hexanol.

In a preferred embodiment of the invention and/or embodiments thereof residue in step (a) R of Formula (2A) is ethyl and the organic solvent is selected from ethanol, 2-propanol, 1-butanol, 1-pentanol, 1-hexanol and mixtures thereof.

Alternatively preferred in step (a) residue R of Formula (2A) is ethyl and the organic solvent is ethanol, or residue R of Formula (2A) is ethyl and the organic solvent is 2-propanol.

Alternatively preferred in step (a) residue R of Formula (2A) is ethyl and the organic solvent is 1-butanol, or residue R of Formula (2A) is ethyl and the organic solvent is 1-pentanol, or residue R of Formula (2A) is ethyl and the organic solvent is 1-hexanol.

In a preferred embodiment of the invention and/or embodiments thereof in step (a) the chiral base is (R)-1-phenyl-2-methyl-propylamine (Formula 2B) and the organic solvent is ethanol, or the chiral base is (R)-1-phenyl-2-methyl-propylamine (Formula 2B) and the organic solvent is 2-propanol, or the chiral base is (R)-1-phenyl-2-methyl-propylamine (Formula 2B) and the organic solvent is 1-butanol, or the chiral base is (R)-1-phenyl-2-methyl-propylamine (Formula 2B) and the organic solvent is 1-pentanol, or the chiral base is (R)-1-phenyl-2-methyl-propylamine (Formula 2B) and the organic solvent is 1-hexanol.

In a preferred embodiment of the invention and/or embodiments thereof in step (a) residue X of Formula (2C) is Cl (chloride) or Br (bromide).

In a preferred embodiment of the invention and/or embodiments thereof in step (a) residue X of Formula (2C) is Cl and the organic solvent is 2-propanol.

In a preferred embodiment of the invention and/or embodiments thereof in step (a) residue X of Formula (2C) is Br and the organic solvent is selected from the group consisting of ethanol, 2-propanol, 1-butanol, 1-pentanol, and mixtures thereof.

In a preferred embodiment of the invention and/or embodiments thereof in step (a) residue X of Formula (2C) is Br and the organic solvent is ethanol, or residue R of Formula (2C) is Br and the organic solvent is 2-propanol, or residue R of Formula (2C) is Br and the organic solvent is 1-butanol, or residue R of Formula (2C) is Br and the organic solvent is 1-pentanol.

In a preferred embodiment of the invention and/or embodiments thereof in step (a) (5RS)-4-[5-(3,5-dichlorophenyl)-5-(trifluoromethyl)-4H-isoxazol-3-yl]-2-methyl-benzoic acid is reacted with a compound of Formula (2A), (2B) or (2C) in an organic solvent having a polarity $E_T(30)$ between 180 and 230 kJ/mol to form a precipitate and a supernatant solution. Thus, in the organic solvent (5RS)-4-[5-(3,5-dichlorophenyl)-5-(trifluoromethyl)-4H-isoxazol-3-yl]-2-methyl-benzoic, preferably (S)-4-[5-(3,5-dichlorophenyl)-5-(trifluoromethyl)-4H-isoxazol-3-yl]-2-methyl-benzoic acid, and a compound of Formula (2A), (2B) or (2C) are acting mutually on each other to form a product which precipitates and a supernatant solution. In other words, (5RS)-4-[5-(3,5-dichlorophenyl)-5-(trifluoromethyl)-4H-isoxazol-3-yl]-2-methyl-benzoic acid, preferably (5S)-4-[5-(3,5-dichlorophenyl)-5-(trifluoromethyl)-4H-isoxazol-3-yl]-2-methyl-benzoic acid, and a compound of Formula (2A), (2B) or (2C) react with each other to form a solid product which can precipitate, preferably completely precipitate, from the reaction mixture, while a supernatant solution remains. Said supernatant solution preferably contains a small part of the unreacted (5S)-4-[5-(3,5-dichlorophenyl)-5-(trifluoromethyl)-4H-isoxazol-3-yl]-2-methyl-benzoic acid, and preferably a large part of (5R)-4-[5-(3,5-dichlorophenyl)-5-(trifluoromethyl)-4H-isoxazol-3-yl]-2-methyl-benzoic acid.

In an alternative preferred embodiment of the invention and/or embodiments in step (a) of the method of the present invention the organic solvent has an $E_T(30)$ value between 130 and 175 kJ/mol.

Examples of solvents having an $E_T(30)$ value between 130 and 175 kJ/mol are aliphatic, cycloaliphatic or aromatic ethers such as ethylene glycol dimethyl ether, triethylene glycol dimethyl ether, 1,2-dimethoxyethane, di-n-butyl ether, di-tert.butyl ether, di-iso-propyl ether, n-butyl methyl ether, methyl tert-butyl ether, cyclopentyl methyl ether, dioxane, tetrahydropyran, 2,2,5,5-tetramethyltetrahydropyran, tetrahydrofuran, tetra-hydro-2-methylfuran, 2,2,5,5-tetramethyltetrahydrofuran, benzyl methyl ether, dibenzyl ether, anisole, 3-methyl anisole and phenetole; arenes and pyridines such as benzene, toluene, m-xylene and mesitylene; haloarenes such as chlorobenzene, 1,3-dichlorobenzene, bromobenzene and 1,3 dibromobenzene and pyridine; aliphatic esters such as methyl formate, methyl acetate, methyl propanoate, methyl butanoate, methyl hexanoate, ethyl formate, ethyl acetate, ethyl propanoate, ethyl benzoate and butyl acetate; aliphatic, cycloalipatic or aromatic amines such as diethylamine, triethylamine, diisopropylamine, morpholine, piperidine; haloalkanes such as trichloromethane, tetrachloromethane, 1,1-dichloroethane, 1,2-dichloroethane and 1,1,2,2-tetrachlorethane and mixtures thereof.

In a preferred embodiment of the invention and/or embodiments thereof the organic solvent in step (a) has an $E_T(30)$ value between 132 and 175 kJ/mol. Preferably between 134 and 174 kJ/mol, more preferably 135 and 170 kJ/mol, in particular between 140 and 165, and more in particular between 134 and 160 kJ/mol.

In a preferred embodiment of the invention and/or embodiments thereof the organic solvent in step (a) is an aliphatic or cycloaliphatic ether such as ethylene glycol dimethyl ether, triethylene glycol dimethyl ether, 1,2-dimethoxyethane, di-n-butyl ether, di-tert-butyl ether, di-isopropyl ether, n-butyl methyl ether, methyl tert-butyl ether, cyclopentyl methyl ether, dioxane, tetrahydrofuran, tetrahydro-2-methylfuran; an arene such as benzene, toluene, m-xylene, mesitylene, a haloarene such as chlorobenzene, bromobenzene; an aliphatic ester such as methyl acetate, methyl propanoate, methyl butanoate, ethyl acetate, ethyl propanoate, ethyl benzoate, butyl acetate; an aliphatic amine such as diethylamine, triethylamine, diisopropylamine; a haloalkane such as trichloromethane, tetrachloromethane, 1,1 dichloroethane and 1,2-dichloroethane and mixtures thereof.

In a preferred embodiment of the invention and/or embodiments thereof the organic solvent in step (a) is selected from the group consisting of methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof the organic solvent in step (a) is methyl tert-butyl ether. In a preferred embodiment of the invention and/or embodiments thereof the organic solvent in step (a) is cyclopentyl methyl ether. In a preferred embodiment of the invention and/or embodiments thereof the organic solvent in step (a) is tetrahydrofuran. In a preferred embodiment of the invention and/or embodiments thereof the organic solvent in step (a) is dioxane. In a preferred embodiment of the invention and/or embodiments thereof the organic solvent in step (a) is chlorobenzene. In a preferred embodiment of the invention and/or embodiments thereof the organic solvent in step (a) is toluene. In a preferred embodiment of the invention and/or embodiments thereof the organic solvent in step (a) is m-xylene. In a preferred embodiment of the invention and/or embodiments thereof the organic solvent in step (a) is mesitylene. In a preferred embodiment of the invention and/or embodiments thereof the organic solvent in step (a) is ethyl acetate. In a preferred embodiment of the invention and/or embodiments thereof the organic solvent in step (a) is butyl acetate. In a preferred embodiment of the invention and/or embodiments thereof the organic solvent in step (a) is triethylamine. In a preferred embodiment of the invention and/or embodiments thereof the organic solvent is in step (a) trichloromethane. In a preferred embodiment of the invention and/or embodiments thereof the organic solvent in step (a) is 1,2-dichloroethane.

In a preferred embodiment of the invention and/or embodiments thereof the organic solvent in step (a) is selected from the group consisting of methyl tert-butyl ether, cyclopenty methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue R of Formula (2A) is methyl and the organic solvent is selected from the group consisting of methyl tertbutyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue R of Formula (2A) is methyl and the organic solvent is selected from the group consisting of methyl tertbutyl ether, cyclopentyl methyl ether, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) R residue of Formula (2A) is methyl and the organic solvent is selected from the group consisting of dioxane, chlorobenzene, toluene, ethyl acetate, butyl acetate, triethylamine, trichloromethane, 1,2-dichloroethane and mixtures thereof.

In a preferred embodiment of the invention and/or embodiments thereof in step (a) residue R of Formula (2A) is methyl and the organic solvent is methyl tert-butyl ether, or residue R of Formula (2A) is methyl and the organic solvent is cyclopentyl methyl ether, or residue R of Formula (2A) is methyl and the organic solvent is tetrahydrofuran, or residue R of Formula (2A) is methyl and the organic solvent is dioxane, or residue R of Formula (2A) is methyl and the organic solvent is chlorobenzene, or residue R of Formula (2A) is methyl and the organic solvent is toluene, or residue R of Formula (2A) is methyl and the organic solvent is m-xylene, or residue R of Formula (2A) is methyl and the organic solvent is mesitylene, or residue R of Formula (2A) is methyl and the organic solvent is ethyl acetate, or residue R of Formula (2A) is methyl and the organic solvent is butyl acetate, or residue R of Formula (2A) is methyl and the organic solvent is triethylamine, or residue R of Formula (2A) is methyl and the organic solvent is trichloromethane or residue R of Formula (2A) is methyl and the organic solvent is 1,2-dichloroethane.

In a preferred embodiment of the invention and/or embodiments thereof in step (a) residue R of Formula (2A) is ethyl and the organic solvent is selected the group consisting of methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue R of Formula (2A) is ethyl and the organic solvent is selected the group consisting of methyl tert-butyl ether, cyclopentyl methyl ether, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue R of Formula (2A) is ethyl and the organic solvent is selected the group consisting of methyl tert-butyl ether, cyclopentyl methyl ether, dioxane, chlorobenzene, toluene, m-xylene, mesitylene, ethyl acetate, butyl acetate, triethylamine, 1,2-dichloroethane and mixtures thereof.

In a preferred embodiment of the invention and/or embodiments thereof in step (a) residue R of Formula (2A) is ethyl and the organic solvent is selected the group consisting of methyl tert-butyl ether, cyclopentyl methyl ether, chlorobenzene, m-xylene, mesitylene, ethyl acetate, butyl acetate, triethylamine, 1,2-dichloroethane and mixtures thereof.

In a preferred embodiment of the invention and/or embodiments thereof, in step (a) residue R of Formula (2A) is ethyl and the organic solvent is methyl tert-butyl ether, or residue R of Formula (2A) is ethyl and the organic solvent is cyclopentyl methyl ether, or residue R of Formula (2A) is ethyl and the organic solvent is tetrahydrofuran, or residue R of Formula (2A) is ethyl and the organic solvent is dioxane, or residue R of Formula (2A) is ethyl and the organic solvent is chlorobenzene, or residue R of Formula (2A) is ethyl and the organic solvent is toluene, or residue R of Formula (2A) is ethyl and the organic solvent is m-xylene, or residue R of Formula (2A) is ethyl and the organic solvent is mesitylene, or residue R of Formula (2A) is ethyl and the organic solvent is ethyl acetate, or residue R of Formula (2A) is ethyl and the organic solvent is butyl acetate, or residue R of Formula (2A) is ethyl and the organic solvent is triethylamine, or residue R of Formula (2A) is ethyl and the organic solvent is trichloromethane or residue R of Formula (2A) is ethyl and the organic solvent is 1,2-dichloroethane.

In a preferred embodiment of the invention and/or embodiments thereof in step (a) the chiral base is (R)-1-phenyl-2-methyl-propylamine (Formula 2B) and the organic solvent is tetrahydrofuran, or the chiral base is (R)-1-phenyl-2-methyl-propylamine (Formula 2B) and the organic solvent is dioxane, or the chiral base is (R)-1-phenyl-2-methyl-propylamine (Formula 2B) and the organic solvent is toluene, or the chiral base is (R)-1-phenyl-2-methyl-propylamine (Formula 2B) and the organic solvent is ethyl acetate, or the chiral base is (R)-1-phenyl-2-methyl-propylamine (Formula 2B) and the organic solvent is 1,2-dichloroethane.

In a preferred embodiment of the invention and/or embodiments thereof in step (a) the chiral base is (R)-1-phenyl-2-methyl-propylamine (Formula 2B) and the organic solvent is selected from the group consisting of methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) the chiral base is (R)-1-phenyl-2-methyl-propylamine (Formula 2B) and the organic solvent is selected from the group consisting of methyl tert-butyl ether, cyclopentyl methyl ether, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) the chiral base is (R)-1-phenyl-2-methyl-propylamine (Formula 2B) and the organic solvent is selected from the group consisting of chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) the chiral base is (R)-1-phenyl-2-methyl-propylamine (Formula 2B) and the organic solvent is selected from the group consisting of chlorobenzene, toluene, ethyl acetate, butyl acetate, triethylamine, trichloromethane, 1,2-dichloroethane and mixtures thereof.

In a preferred embodiment of the invention and/or embodiments thereof in step (a) residue X of Formula (2C) is Cl (chloride) or Br (bromide).

In a preferred embodiment of the invention and/or embodiments thereof in step (a) residue X of Formula (2C) is Cl and the organic solvent is selected from the group consisting of tetrahydrofuran, dioxane, toluene, ethyl acetate and mixtures thereof.

In a preferred embodiment of the invention and/or embodiments thereof in step (a) residue X of Formula (2C) is Cl and the organic solvent is selected from the group consisting of methyl tert-butyl ether, cyclopentyl methyl ether, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue X of Formula (2C) is Cl and the organic solvent is selected from the group consisting of methyl tert-butyl ether, cyclopentyl methyl ether, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue X of Formula (2C) is Cl and the organic solvent is selected from the group consisting of chlorobenzene, toluene, ethyl acetate, butyl acetate, triethylamine, trichloromethane, 1,2-dichloroethane and mixtures thereof.

In a preferred embodiment of the invention and/or embodiments thereof in step (a) residue X of Formula (2C) is Cl and the organic solvent is selected from the group consisting of toluene, ethyl acetate and mixtures thereof.

In a preferred embodiment of the invention and/or embodiments thereof in step (a) residue R of Formula (2C) is chloride and the organic solvent is tetrahydrofuran, residue R of Formula (2C) is chloride and the organic solvent is dioxane, residue R of Formula (2C) is chloride and the organic solvent is toluene, or residue R of Formula (2C) is chloride and the organic solvent is ethyl acetate.

In a preferred embodiment of the invention and/or embodiments thereof in step (a) residue X of Formula (2C) is Br and the organic solvent is selected from the group consisting of tetrahydrofuran, dioxane, toluene, ethyl acetate and mixtures thereof.

In a preferred embodiment of the invention and/or embodiments thereof in step (a) residue R of Formula (2C) is bromide and the organic solvent is tetrahydrofuran, residue R of Formula (2C) is bromide and the organic solvent is dioxane, residue R of Formula (2C) is bromide and the organic solvent is toluene, or residue R of Formula (2C) is bromide and the organic solvent is ethyl acetate.

In a preferred embodiment of the invention and/or embodiments thereof in step (a) residue X of Formula (2C) is Br and the organic solvent is selected from the group consisting of methyl tert-butyl ether, cyclopentyl methyl ether, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue X of Formula (2C) is Br and the organic solvent is selected from the group consisting of methyl tert-butyl ether, cyclopentyl methyl ether, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof in step (a) residue X of Formula (2C) is Br and the organic solvent is selected from the group consisting of chlorobenzene, toluene, ethyl acetate, butyl acetate, triethylamine, trichloromethane, 1,2-dichloroethane and mixtures thereof.

In a preferred embodiment of the invention and/or embodiments thereof in step (a) residue X of Formula (2C) is Br and the organic solvent is selected from the group consisting of toluene, ethyl acetate and mixtures thereof.

In a preferred embodiment of the invention and/or embodiments thereof in step (a) (5RS)-4-[5-(3,5-dichlorophenyl)-5-(trifluoromethyl)-4H-isoxazol-3-yl]-2-methyl-benzoic acid is reacted with a compound of Formula (2A), (2B) or (2C) in an organic solvent having a polarity $E_T(30)$ between 130 and 175 kJ/mol to form a precipitate and a supernatant solution. Thus, in the organic solvent (5RS)-4-[5-(3,5-dichlorophenyl)-5-(trifluoromethyl)-4H-isoxazol-3-yl]-2-methyl-benzoic, preferably (S)-4-[5-(3,5-dichlorophenyl)-5-(trifluoromethyl)-4H-isoxazol-3-yl]-2-methyl-benzoic acid, and a compound of Formula (2A), (2B) or (2C) are acting mutually on each other to form a product which precipitates and a supernatant solution. In other words, (5RS)-4-[5-(3,5-dichlorophenyl)-5-(trifluoromethyl)-4H-isoxazol-3-yl]-2-methyl-benzoic acid, preferably (5S)-4-[5-(3,5-dichlorophenyl)-5-(trifluoromethyl)-4H-isoxazol-3-yl]-2-methyl-benzoic acid, and a compound of Formula (2A), (2B) or (2C) react with each other to form a solid product which can precipitate, preferably completely precipitate, from the reaction mixture, while a supernatant solution remains. Said supernatant solution preferably contains a small part of the unreacted (5S)-4-[5-(3,5-dichlorophenyl)-5-(trifluoromethyl)-4H-isoxazol-3-yl]-2-methyl-benzoic acid, and preferably a large part of (5R)-4-[5-(3,5-dichlorophenyl)-5-(trifluoromethyl)-4H-isoxazol-3-yl]-2-methyl-benzoic acid.

Reacting (5RS)-4-[5-(3,5-dichlorophenyl)-5-(trifluoromethyl)-4H-isoxazol-3-yl]-2-methyl-benzoic acid with a compound of Formula (2A), (2B) or (2C) can be carried out at any temperature as long as the solvent is in a liquid state. For example, in step (a) the reaction can be carried out at a temperature between 4 and 65° C., preferably between 10 and 55° C., also preferred between 15 and 45° C., preferably between 20 and 40° C., preferably between 25 and 35° C., and most preferred at about 23° C. (also referred to as room temperature).

In a preferred embodiment of the invention and/or embodiments thereof step (a) comprises heating (5RS)-4-[5-(3,5-dichlorophenyl)-5-(trifluoromethyl)-4H-isoxazol-3-yl]-2-methyl-benzoic acid with a compound of Formula (2A), (2B) or (2C) to an elevated temperature. An elevated temperature is a temperature from 23° C. (room temperature) to the boiling temperature of the organic solvent, preferably from 30° C. to the boiling temperature of the organic solvent minus 5° C., more preferably from 40° to the boiling temperature of the organic solvent minus 20° C. That means that in case ethanol with a boiling temperature or boiling point of 78° C. is used as organic solvent, the reaction in step (i)) can be preferably carried out at from 23° C. to 78° C., preferably from 30° C. to 73° C., more preferably from 40° C. to 68° C. All temperatures as indicated herein and relating to boiling temperatures or boiling points relate to temperatures measured at normal pressure of 101 kPa.

Further, step (a) preferably comprises cooling the reacting mixture of said step. In case that step (a) does not comprise heating the reacting mixture to an elevated temperature, the reaction mixture can be cooled to 0° C. to 20° C., preferably about 10° C. In case that step (i) comprises heating the reaction mixture to an elevated temperature, the reaction mixture can be preferably cooled down to 0° C. to 40° C., preferably 10° C. to 30° C., in particular to about 23° C. (room temperature). By cooling the reaction mixture the obtained product forms a precipitate and a supernatant solution, wherein the supernatant solution preferably comprises (5R)-4-[5-(3,5-dichlorophenyl)-5-(trifluoromethyl)-4H-isoxazol-3-yl]-2-methyl-benzoic acid, preferably in an enantiomeric excess.

Further, the reaction of step (a) can be preferably subjected to a mechanical movement such as stirring or ultrasonic treatment.

In a preferred embodiment of the invention and/or embodiments thereof the duration of step (a) can be between 15 minutes and 24 hours, preferably between 30 minutes and 12 hours, in particular between 1 hour and 6 hours.

In step (b) the supernatant solution from step (a) is separated from the precipitate. The supernatant solution is a liquid and can be separated from the solid precipitate by any method for separating a liquid from a solid. Examples of these methods are decanting or pouring off the supernatant solution, optionally with a preceding centrifugation step, and filtration.

In a preferred embodiment of the invention and/or embodiments thereof in step (b) the separation of the supernatant solution from the precipitate is carried out via filtration. A filtration as used herein is a mechanical or physical operation that separates a solid, in the present case the precipitate, from a liquid, in the present case the supernatant solution, via a medium through which only the fluid can pass. Such a medium might be referred to as a filter or sieve, preferably a filter. Examples of suitable filters are suction filters, press filters or folded filters, preferably suction filters.

In a preferred embodiment of the invention and/or embodiments thereof the organic solvent in steps (a) and (i) is the same. As far as the definition of the organic solvent is concerned, the same applies as described under step (a) of the present method. In a preferred embodiment of the invention and/or embodiments the organic solvent is 2-propanol.

It unexpectedly turned out that the separation of (S)-IOBA and racemisation of the resulting supernatant solution containing an excess of (R)-IOBA can be carried out in the same solvent, i.e. it is not necessary to change the solvent for carrying out a racemisation step which can be regarded as a recycling step for the valuable (S)-enantiomer of IOBA from a solution with an enantiomeric excess of the (R)-enantiomer of IOBA.

In line with the application the enantiomeric excess (ee) is defined as the absolute difference between the mole fraction of each enantiomer and can be expressed as a percent enantiomeric excess, which is calculated according to the equation:

$$ee=(|F_R-F_S|\times 100)\%$$

wherein
$F_R$ is the mole fraction of the (R)-enantiomer, and
$F_S$ is the mole fraction of the (S)-enantiomer The amount and thus the mole fraction of the corresponding enantiomer can be determined by the methods as known in the art, for example via the numerical value of the optical purity of the compound in question, via chiral column chromatography (chiral LC or SFC) or via NMR-spectroscopy in the presence of chiral shift reagents. In the present application chiral LC mole fraction of the corresponding enantiomer is determined by chiral LC. Other possibilities are the transformation of the (S)-IOBA with chiral amines or alcohols into diastereoisomeric amides or esters and determination of the ee % via LC.

The invention will now be further described by the following, non-limiting examples:

EXAMPLES

Example 1

A flask equipped with a condenser and a thermometer was charged with 2-propanol (12.5 ml) and water (0.85 ml). Solid potassium hydroxide (0.671 g, 11.96 mmol) was dissolved in the solvent and (5R)-4-(5-(3,5-dichlorophenyl)-5-(trifluoromethyl)-4H-isoxazol-3-yl)-2-methylbenzoic acid with 87.2% ee (1 g, 2.391 mmol) was added at 23° C. (room temperature). The mixture was heated to 80° C.

A 50 µl sample was taken after 1 hour, 2 hours and 16 hours, respectively, for determining the degree of racemisation. Each of the samples was treated as follows: It was quenched with $KHSO_4$-solution (1 ml, 2.3 M) and extracted twice with ethyl acetate (once with 2 ml and once with 1 ml). The combined organic phases were concentrated under reduced pressure. The residue was dried under oil-pump vacuum and dissolved in a mixture of i-hexane:ethanol 1:1 (1 ml).

The resulting (R)-IOBA has an enantiomeric excess of 84.8% after one hour, of 84.5% after two hours and of 64% after 16 hours.

Example 2

A flask equipped with a condenser and a thermometer was charged with 2-propanol (6.67 ml) and (5R)-4-(5-(3,5-dichlorophenyl)-5-(trifluoromethyl)-4H-isoxazol-3-yl)-2-methylbenzoic acid with 86.4% ee (1 g, 2.391 mmol) was dissolved. Sodium hydroxide (0.393 g, 9.83 mmol) micro pearls were added at 40° C. and the mixture was heated to reflux, whereby a yellow-coloured suspension resulted.

A 50 µl sample was taken after 2 hours, 4 hours and 20 hours, respectively, for determining the degree of racemisation. Each of the samples was treated as described in Example 1.

The resulting (R)-IOBA has an enantiomeric excess of 62.4% after two hours, of 85.0% after four hours and of 31.8% after 20 hours.

Example 3

A solution of (5R)-4-(5-(3,5-dichlorophenyl)-5-(trifluoromethyl)-4H-isoxazol-3-yl)-2-methylbenzoic acid with >99% ee (50 mg, 0.120 mmol) in 2-propanol (299 µl) was incubated with a 2-propanol solution of potassium hydroxide (20.38 µl, 0.359 mmol) in a 1 ml conical vial. The mixture was heated to 90° C. overnight.

A sample of 100 µL of the reaction mixture was concentrated to a solid, diluted with 2 ml aqueous $KHSO_4$ (15%) and extracted with 1 to 2 mL ethyl acetate. The organic phase was separated and concentrated. The oil was dried under reduced vacuum and dissolved in i-hexane:ethanol 1:1 (1 mL). From this solution 250 μL were diluted with i-hexane:ethanol 1:1 (1 mL) and analysed via chiral LC-DAD. The resulting (R)-IOBA had an enantiomeric excess of 56.47%.

Example 4

A solution of (R)-4-(5-(3,5-dichlorophenyl)-5-(trifluoromethyl)-4,5-dihydroisoxazol-3-yl)-2-methylbenzoic acid with >99% ee (50 mg, 0.120 mmol) in 2-Propanol (299 μl) was incubated with a 2-propanol solution of cesium hydroxide (66.8 μl, 0.359 mmol) in a 1 mL conical vial. The mixture was heated to 90° C. overnight.

A sample of 100 μL of the reaction mixture was concentrated to a solid, diluted with 2 mL aqueous $KHSO_4$ (15%) and extracted with 1-2 mL ethyl acetate. The organic phase was separated and concentrated. The oil was dried under reduced vacuum and dissolved in i-hexane:ethanol 1:1 (1 mL). From this solution 250 μL were diluted with i-hexane:ethanol 1:1 (1 mL) and analysed via chiral LC-DAD. The resulting (R)-IOBA has an enantiomeric excess of 56.47%.

Example 5

A flask was equipped with a condenser and a thermometer. The flask was charged with 2-propanol (6.67 ml), powdered potassium hydroxide (0.671 g, 11.96 mmol) was dissolved in the solvent and (5R)-4-(5-(3,5-dichlorophenyl)-5-(trifluoromethyl)-4H-isoxazol-3-yl)-2-methylbenzoic acid with 87.2% ee (1 g, 2.391 mmol) was added at 40° C. The mixture was heated to reflux. A clear orange solution was formed. After a while, a yellow-coloured solid material precipitated. The suspension was further heated to reflux. A 50 μL-sample of the suspension was worked up as described in Example 1. The resulting (R)-IOBA had an enantiomeric excess of 0.8%.

As can be seen from Examples 1 to 5, the excess of (R)-IOBA contained in the resulting product is reduced. Thus, it can be concluded that the molar amount of (S)-IOBA is enhanced by racemizing the starting mixture.

Example 6

A 1 L three neck flask equipped with a KPG-stirring unit (IKA RW-16 basic), and a reflux condenser was charged with 2-propanol (200 mL) and (5RS)-4-(5-(3,5-dichlorophenyl)-5-(trifluoromethyl)-4H-isoxazol-3-yl)-2-methylbenzoic acid (100 g, 239 mmol). Another portion of 2-propanol (250 mL) was added. The mixture was stirred until all the solid material has been dissolved. (S)-1-phenylpropylamine (21 ml, 144 mmol) was added quickly in 1 mL (first) and 20 mL (second) portions via a syringe.

The mixture was further stirred for 75 min at RT, after which a suspension was formed. The mixture was stirred for 45 min at reflux temperature. The heating was turned off and the suspension slowly cooled down to room temperature under stirring.

The suspension was filtrated, and the colorless filtercake was washed with 4× in 100 mL 2-propanol. The filtercake was dried overnight under reduced pressure.

Amount of the isolated (S)-IOBA-(S)-1-phenylpropylammonium salt: 57.065 g (yield: 86.3%). The chiral LC analysis of a sample of the ammonium salt showed that the enantioenriched (S)-IOBA has an enantiomeric excess of 95% without further crystallization.

Recycling Step:

The collected supernatant and the washing solutions from the crystallisation step were concentrated to 400 mL. The enantio-enriched (R)-IOBA solution was charged with powdered potassium hydroxide (27.916 g, 498 mmol) and heated to reflux under stirring. Samples were taken from the reaction mixture and were analyzed by chiral LC in order to determine the enantiomeric excess of the (R)-IOBA. Heating was stopped when the residual enantiomeric excess of the (R)-IOBA reached 2.4%.

The solvent was evaporated and the remaining IOBA-salt was charged with 300 mL water. A solution of conc. $H_2SO_4$ (13.3 mL) in 65 mL water was added under stirring. The aqueous suspension was set to pH=2 with an additional volume of conc. $H_2SO_4$ (3.8 mL) in 18.5 mL water. The aqueous suspension was consecutively extracted with 1×200 mL and 2×100 mL of ethyl acetate. The collected organic phases were washed 2× with brine (100 mL) and dried over $MgSO_4$. After filtration, the organic solvent was evaporated in order to obtain the recycled IOBA as a solid material. Amount of IOBA after drying: 53 g containing 7 wt % ethyl acetate.

The invention claimed is:

1. A Method for racemizing a mixture containing (5R)-4-[5-(3,5-dichlorophenyl)-5-(trifluoromethyl)-4H-isoxazol-3-yl]-2-methyl-benzoic acid according to Formula (1a) and (5S)-4-[5-(3,5-dichlorophenyl)-5-(trifluoromethyl)-4H-isoxazol-3-yl]-2-methyl-benzoic acid according to Formula (1b)

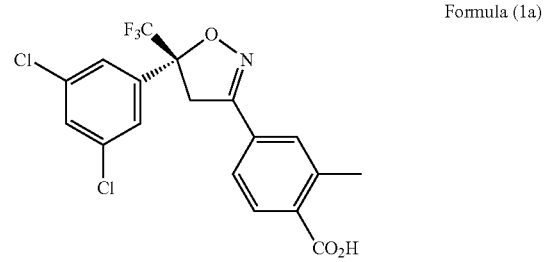 [SMILES: Cc1cc(C2=NOC(c3cc(Cl)cc(Cl)c3)(C(F)(F)F)C2)ccc1C(=O)O]

Formula (1a)

and

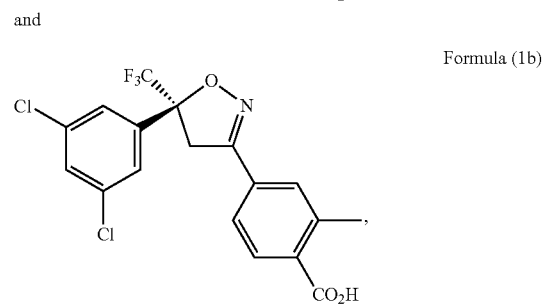

Formula (1b)

wherein the mixture has an enantiomeric excess of the compound according to Formula (1a) comprising the step of:
(i) reacting the mixture with an alkaline compound in an organic solvent obtaining a reacted mixture
wherein step (i) is carried out in the absence of phase transfer catalysts and wherein the organic solvent is 2 propanol and wherein the alkaline compound is potassium hydroxide, cesium hydroxide or potassium tert-butanolate.

2. The Method according to claim 1, further comprising the steps of:
(ii) acidifying the reacted mixture from step (i), to form a result mixture and (iii) separating the result mixture from step (ii) into a compound mixture and supernatant.

3. The Method according to claim 1, further comprising the preceding steps of (a) reacting (5RS)-4-[5-(3,5-dichlorophenyl)-5-(trifluoromethyl)-4H-isoxazol-3-yl]-2-methyl-benzoic acid with a compound of Formula (2A), (2B) or (2C)

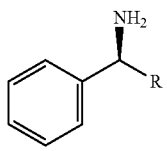

Formula (2A)

wherein R is an alkyl with 1 or 2 carbon atoms,

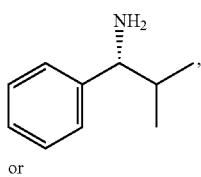

Formula (2B)

or

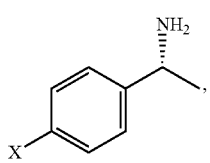

Formula (2C)

wherein X is Cl or Br;
in an organic solvent is 2-propanol to form a precipitate and a supernatant solution, and
(b) separating the supernatant solution containing the mixture containing (5R)-4-[5-(3,5-dichlorophenyl)-5-(trifluoromethyl)-4H-isoxazol-3-yl]-2-methyl-benzoic acid according to Formula (1a) and (5S)-4-[5-(3,5-dichlorophenyl)-5-(trifluoromethyl)-4H-isoxazol-3-yl]-2-methyl-benzoic acid according to Formula (1b) from the precipitate.

4. The Method according to claim 3, wherein in step (a) R of Formula (2A) is methyl or R of Formula (2A) is ethyl.

5. The Method according to claim 3, wherein step (a) comprises heating (5RS)-4-[5-(3,5-dichlorophenyl)-5-(trifluoromethyl)-4H-isoxazol-3-yl]2-methyl-benzoic acid with the compound of Formula (2A), (2b) or (2C) in the solvent to an elevated temperature.

6. The Method according to claim 3, wherein in step (b) the separation of the supernatant solution from step (a) from the precipitate is carried out via filtration.

7. The method according to claim 2, further comprising the preceding steps of
(a) reacting (5RS)-4-[5-(3,5-dichlorophenyl)-5-(trifluoromethyl)-4H-isoxazol-3-yl]-2-methyl-benzoic acid with a compound of Formula (2A), (2B) or (2C)

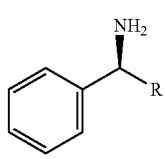

Formula (2A)

wherein R is an alkyl with 1 or 2 carbon atoms,

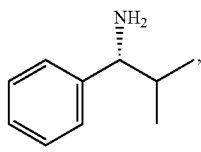

Formula (2B)

or

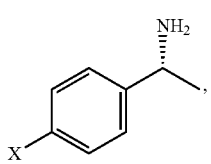

Formula (2C)

wherein X is Cl or Br;
in an organic solvent is 2-propanol to form a precipitate and a supernatant solution, and
(b) separating the supernatant solution containing the mixture containing (5R)-4-[5-(3,5-dichlorophenyl)-5-(trifluoromethyl)-4H-isoxazol-3-yl]-2-methyl-benzoic acid according to Formula (1a) and (5S)-4-[5-(3,5-dichlorophenyl)-5-(trifluoromethyl)-4H-isoxazol-3-yl]-2-methyl-benzoic acid according to Formula (1b) from the precipitate.

8. The method according to claim 7, wherein in step (a) R of Formula (2A) is methyl or R of Formula (2A) is ethyl.

* * * * *